US00PP22762P3

(12) United States Plant Patent
Lee

(10) Patent No.: US PP22,762 P3
(45) Date of Patent: May 29, 2012

(54) AZALEA PLANT NAMED 'ROBLES'

(50) Latin Name: ***Rhododendron* hybrid**
Varietal Denomination: Robles

(75) Inventor: Robert Edward Lee, Independence, LA (US)

(73) Assignee: Plant Development Sevices, Inc., Loxley, AL (US)

( * ) Notice: Subject to any disclaimer, the term of this patent is extended or adjusted under 35 U.S.C. 154(b) by 241 days.

(21) Appl. No.: 12/662,365

(22) Filed: Apr. 13, 2010

(65) Prior Publication Data

US 2011/0252515 P1 Oct. 13, 2011

(51) Int. Cl.
*A01H 5/00* (2006.01)

(52) U.S. Cl. ..... Plt./238

(58) Field of Classification Search ..... Plt./238
See application file for complete search history.

(56) References Cited

U.S. PATENT DOCUMENTS

PP10,438 P * 6/1998 Lee ..... Plt./240

OTHER PUBLICATIONS

Anonymous. "Autumn Lilac" Encore Azalea.com available at: http://www.encoreazalea.com/medium/autumn-lilac-new-for-spring-2010.*

* cited by examiner

*Primary Examiner* — Wendy C Haas
(74) *Attorney, Agent, or Firm* — Breiner & Breiner, L.L.C.

(57) ABSTRACT

A new and distinct variety of Azalea plant named 'Robles', characterized by its unique blooming time, dense and globose growth habit, and single, large, attractive purple flowers is disclosed.

1 Drawing Sheet

Genus species: *Rhododendron* hybrid.
Varietal denomination: 'Robles'.

FIELD OF INVENTION

The present invention relates to a new and distinct variety of evergreen Azalea of the genus *Rhododendron* and a member of the Ericaceae family. This new Azalea variety, hereinafter referred to as 'Robles', was discovered by Robert Edward Lee in August, 1998 in Independence, La. 'Robles' is characterized by its unique blooming time, dense and globose growth habit, and single, large, attractive purple flowers.

BACKGROUND OF THE INVENTION

'Robles' originated from a controlled breeding program in Independence, La. and was subsequently tested and evaluated primarily in Independence, La. and Loxley, Ala. The references in this application to these various evaluations will refer primarily to these two locations. The objective of the breeding program was to create new Azalea varieties which have unique blooming periods, bloom colors, bloom forms, bloom sizes, and growth habits. 'Robles' originated from a cross made by Mr. Lee in April, 1996 of the cultivar 'Watchet' (unpatented) as the female, or seed, parent with the Azalea hybrid 'Conleb', U.S. Plant Pat. No. 10,581 as the male, or pollen, parent.

Asexual propagation of the new plant by cuttings has been under Mr. Lee's direction and control in Independence, La. and Loxley, Ala. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices.

1. Unique spring, summer, and fall blooming.
2. A purple flower color Purple-Violet Group 81C with dotting color Purple-Violet Group 80A.
3. Large, single flowers ranging in size from 2¾" (6.9 cm) to 3¼" (8.2 cm) in diameter.
4. Easily propagated with semi-hardwood cuttings in late spring through the summer.
5. Fast growth rate under normal fertilization and moisture conditions.
6. Dense and globose in nature.
7. Good specimen plant.
8. Desirable in planters.
9. Makes a very good hedge or screen.
10. Very good foundation plant.
11. Does well as an understory plant in a woodland garden.
12. Hardy to Zone 7.
13. Attracts butterflies.

DESCRIPTION OF THE DRAWINGS

This new Azalea hybrid variety is illustrated by the accompanying photographic prints in which.

Figure 1:
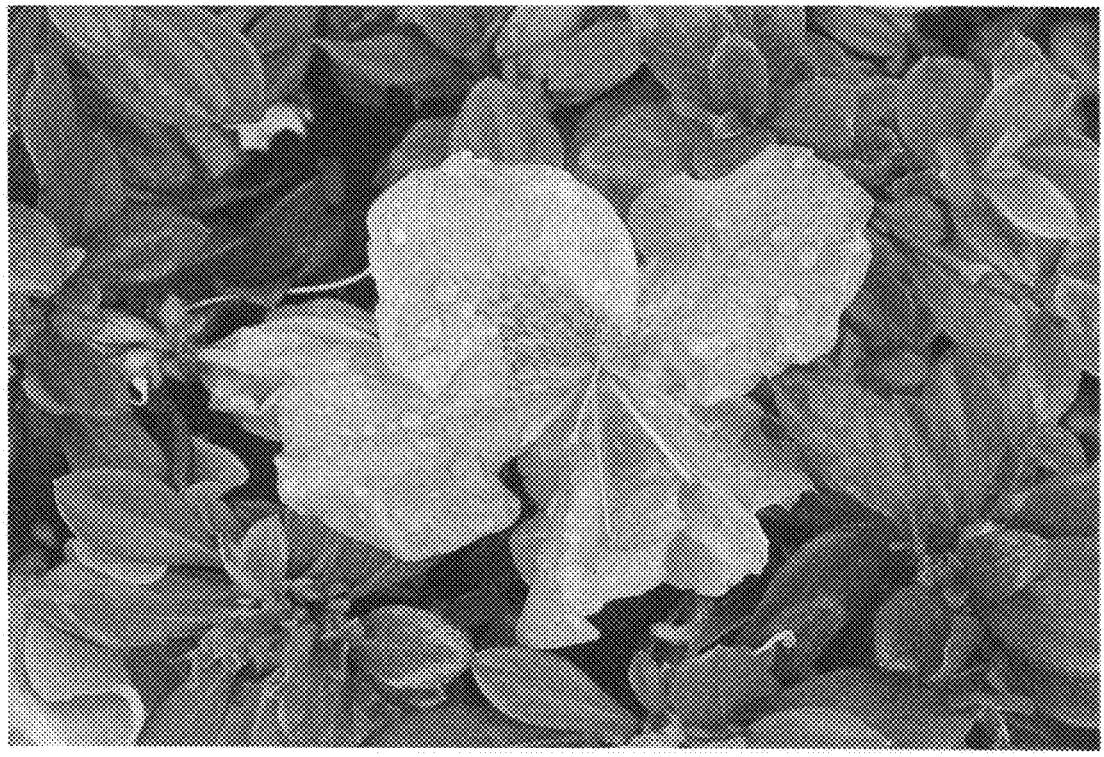
FIG. 1 is a photograph of a close-up showing flower, foliage, and stem color, as well as flower size and form of the new Azalea hybrid cultivar of the present invention.
Figure 2:
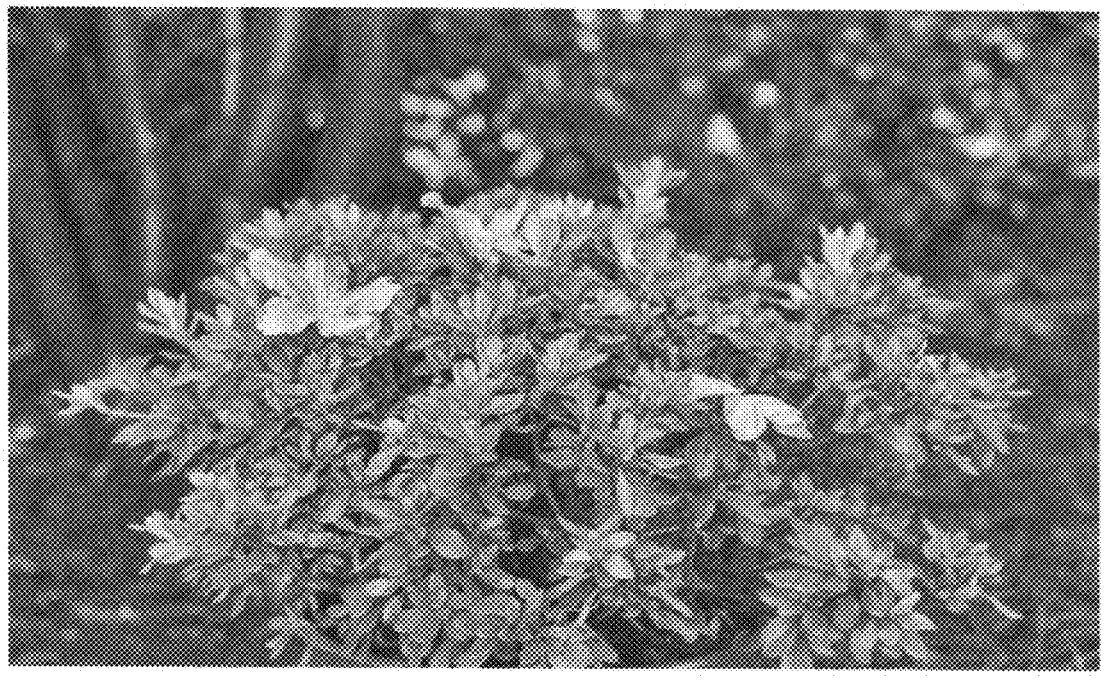
FIG. 2 is a photograph showing the dense and globose growth habit of a young three gallon plant of the new Azalea hybrid cultivar of the present invention.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart, 2001 version. Description of colors in ordinary terms are presented where appropriate for clarity in meaning.

BOTANICAL DESCRIPTION OF THE PLANT

The following is a detailed description of the new variety of Azalea based on observations made of two year old plants grown in three gallon containers in wholesale commercial production practices, in greenhouses, and in established landscape plantings.

Distinctive characteristics:

TABLE 1

| Characteristic | 'Robles' | 'Watchet' | 'Conleb' U.S. Plant Pat. No. 10,581 | *R. oldhamii* 'Fourth of July' |
|---|---|---|---|---|
| Height (Mature) | 3-4' (0.9-1.2 m) | 2-3' (0.6-0.9 m) | 4-5' (1.2-1.5 m) | 8-10' (2.4-3 m) |
| Width (Mature) | 3-4' (0.9-1.2 m) | 3-4' (0.9-1.2 m) | 5-6' (1.5-1.8 m) | 6-7' (1.8-2.1 m) |
| Flower Diameter | 2¾-3¼" (6.9-8.2 cm) | 3½-3¾" (8.9-9.4 cm) | 2½-2¾" (6.3-6.9 cm) | 1¾-2¼" (4.4-5.6 cm) |
| Flower Form | Single | Single | Single/semi-double | Single |
| Flower Color | Purple-Violet G. 81C | Red G.49B | Red G. 44A | Red G. 39A |
| Flowers per Terminal | 2-3 | 1-2 | 2-3 | 2-4 |
| Bloom Period | April | May | April | Late June > Frost |
| Bloom Period | Late July > Frost | | Late July > Frost | |
| Petal/Petaloid Number | 5 | 5 | 5-14 | 5 |
| Hardy Zone | 7 | 6 | 7 | 7 |
| Stamen Number | 8-10 | 10 | 0-9 | 7-10 |
| Stamen Type | Non-Petaloid | Non-Petaloid | Some Petaloid | Non-Petaloid |

The female, or seed parent, of 'Robles' is the Azalea 'Watchet'; a moderate pink, single, late blooming, low compact grower. 'Watchet' is an unpatented Robin Hill Hybrid developed by Robert Gartrell in Wycoff, N.J. Mr. Gartrell started his hybridization in 1937 to produce hardy, late blooming azaleas. 'Watchet' is the result of a cross between the Satsuki Hybrid 'Amagasa' (unpatented) and the Robin Hill Hybrid 'Lady Louise' (unpatented).

The male, or pollen, parent of 'Robles' is the Azalea hybrid 'Conleb', U.S. Plant Pat. No. 10,581, which was the result of Mr. Lee's planned cross hybridization between the Azalea 'Watchet' and *Rhododendron oldhamii* 'Fourth of July' (unpatented). 'Robles' differs from 'Conleb' primarily in flower color.

Robert Edward Lee's hybridization program was conducted with emphasis on species that are not commonly found in the genetic make-up of the present day hybrids. The 'Fourth of July' cultivar which Mr. Lee obtained from Dr. Thornton in 1981 is a heavy summer and fall blooming plant, not like the *Rhododendron* Species Foundation form. The flower buds form on new growth and start blooming about July 1. Mr. Lee used this cultivar to cross with existing hybrids which have a tendency to bloom in the fall and which are also fairly hardy. As expected, the resulting seedlings are heavy summer and fall bloomers with very impressive spring blooms also.

Classification:

*Botanic.*—*Rhododendron* hybrid 'Robles'.

*Form.*—Dense and rounded.

*Height.*—3'-4' (0.9-1.2 m).

*Width.*—3'-4' (0.9-1.2 m).

*Growth habit.*—Dense and globose. Fast growth rate under normal fertilization and moisture conditions.

*Growth rate.*—In a period of six years from a rooted cutting the plant reaches a height of 2 feet (0.6 m) and a spread of 2 feet (0.6 m). The growth rate is normally about 6" (15 cm) to 8" (20 cm) per year; the plant reaches a height of 3' to 4' (0.9-1.2 m) at maturity while maintaining a dense habit due to the abundant branch development.

*Foliage.*—Alternate, simple, evergreen, pubescent, elliptic, and varying in size from 1¼" to 1⅞" (3.1-4.7 cm) long and 9/16" to ¾" (1.4-1.9 cm) wide. The margins are entire, with a petiole 3/16" to ¼" (0.5-0.6 cm) long. Midveins and laterals are impressed on the upper leaf surface and prominent on the underside. The base of the leaf is cuneate to attenuate and the apex is acute to mucronate. The upper surface of the immature leaves is dull, pubescent, and is Yellow-Green Group 144A and the underside is Yellow-Green Group 146D, pubescent, and matte. The upper surface of the mature leaves is Yellow-Green Group 147A, glossy and slightly pubescent and the underside is Yellow-Green Group 146B, matte, and pubescent. The immature petioles, midribs, and veins are Yellow-Green Group 146C. New growth is pubescent. These hairs are initially soft and white and cover both sides of the leaf with a higher concentration on the petioles and veins. They are slightly curled, flat, and range in length from 1/64" to 1/32" (0.05-0.1 cm). As the growth matures much of the leaf pubescence is lost; however, the stems, petioles, and leaf veins retain this pubescence which becomes more setaceous and darker in color (Brown Group 200B) through the growing season. The reduction of pubescence makes the leaf appear darker than Yellow-Green Group 147A. Initial spring growth occurs in March. After the initial spring flush there is almost continuous growth until that fall ending in about late October or early November. When grown in full sun, the internode length of this plant is 3/16" to 9/16" (0.5-1.4 cm); when grown in light shade the internode length is ⅜" to ¾" (0.9-1.9 cm). As would be expected a plant grown in shade results in a taller, less dense plant with larger leaves. The average length of terminal growth of the initial spring flush is about 4" (10 cm) for a plant in full sun and about 6" (15 cm) when grown in shade. This growth should not be trimmed since it will produce flowers starting in late July. As the plant continues to grow through the summer and fall more flower buds are produced, which mature and bloom until frost. This remaining growth produces about 4" to 5" (10-12.5 cm) of height. As cool weather approaches, some of the flower buds become dormant. These buds bloom in April of the next year.

*Stems.*—The young stems are Yellow-Green Group 146C and densely clothed with spreading white glandular hairs. During the second growing season they become Greyed-Green Group 197B, glabrous and rugose. The pith is solid and uniform. Young and older stems are densely branched.

*Buds.*—Tight buds at ½" (1.3 cm) are ovate and acuminate Yellow-Green Group 146D with a hairy pubescence Brown Group 200B. The buds are borne in clusters of 2 to 3, and are sheathed by a pair of modified leaf bracts which are from ¼" to ½" (0.6-1.3cm) long, persistent, and Yellow-Green Group 147A. The pedicel is ¼" to ⅜" (0.6-0.9 cm) long, pubescent, and Yellow Green Group 145B. The calyx is 3/16" to ⅜" (0.5-0.9 cm) long, Yellow-Green Group 144C, funnel shaped, persistent, and pubescent. The five imbricated sepals are lanceolate and joined at the base to form a cup. As the buds swell the bud sheath matures to a Greyed-Orange Group 165A, falls off, and reveals the flower color Purple-Violet Group 81C.

*Flowers.*—Perfect, single, Purple-Violet Group 81C (upper surface and under surface), glabrous, open funnel shaped, 2¾" to 3¼" (6.9-8.2 cm) in diameter by 1¾" to 2¼" (4.4-5.6 cm) in depth, borne on current season's growth, non-fragrant; they last on the plant in the garden 5 to 6 days. There are five true petals which are fused at the base, elliptic, and have wavy margins. These petals are 1¾" to 2⅜" (4.4-5.9 cm) long, ⅞" to 1⅜" (2.2-3.4 cm) wide, and have rounded apexes and entire margins. Three out of five petals are dotted with Purple-Violet Group 80A. There are 8 to 10 non-petaloid stamens which are 1¼" to 1½" (3.1-3.8 cm) long. The filaments are Purple Group 75B, the anthers are Greyed-Orange Group 167B, and the pollen matures to Yellow Group 11B. The pistil is single, non-petaloid, 1¼" to 1⅝" (3.1-4.1 cm) long and Red-Purple Group 68D. The ovary is densely glandular-setose and has five locules. The capsule matures in about 5 months to about ¼" to ½" (0.6-1.3 cm) long; it has a persistent style, is Yellow-Green Group 146B, and contains from 100 to 400 nonwinged seeds. Normally fruit set is not heavy. There is a 2 to 3 week flowering period in April. Flowering resumes in July as the new buds mature and continues until frost which can be as late as November or December. Azaleas blooming at this time of year attract butterflies in profusion.

*Culture.*—Grows well in a wide range of conditions, tolerates sun to shade. Prefers a moist, well-drained soil that is rich in organic matter. Responds well to mulching and medium applications of fertilizer; prefers pH 5.0 to 5.5. Very little pruning is needed; adaptable to container and above ground planters; makes a good foundation plant or informal hedge with excellent foliage and flower contrast. Ideal for coastal regions and warmer parts of Piedmont. Propagated with semi-hardwood cuttings in late spring through the summer.

*Pests.*—Lace wing and spider mites can be a problem.

The exemplary embodiments herein disclosed are not intended to be exhaustive or to unnecessarily limit the scope of the invention. The exemplary embodiments were chosen and described in order to explain the present invention so that others skilled in the art may practice the invention.

It is claimed:

1. A new and distinct variety of Azalea plant named 'Robles' as illustrated and described herein.

* * * * *